US006862475B1

(12) United States Patent
Kroll

(10) Patent No.: US 6,862,475 B1
(45) Date of Patent: Mar. 1, 2005

(54) PEDIATRIC RATE VARYING IMPLANTABLE CARDIAC DEVICE

(75) Inventor: Mark W. Kroll, Simi Valley, CA (US)

(73) Assignee: Pacesetter, Inc., Sylmar, CA (US)

(*) Notice: Subject to any disclaimer, the term of this patent is extended or adjusted under 35 U.S.C. 154(b) by 456 days.

(21) Appl. No.: 10/066,419

(22) Filed: Jan. 30, 2002

(51) Int. Cl.[7] .............................................. A61N 1/362
(52) U.S. Cl. ........................................................ 607/9
(58) Field of Search ...................................... 607/4–28

(56) References Cited

U.S. PATENT DOCUMENTS

| 5,466,254 A | 11/1995 | Helland ...................... 607/123 |
| 5,824,020 A | 10/1998 | Cooper ........................ 607/17 |
| 5,964,788 A | 10/1999 | Greenhut ..................... 607/17 |

OTHER PUBLICATIONS

Macfarlane, P.W., PhD, FESC, et al.; "Effects of Age, Sex, and Race on ECG Interval Measurements", Journal of Electrocardiology, vol. 27 Supplement, pp.: 14–19 (1994).

Heragu, Narakesari P., MBBS et al., "Heart Rate Variability in Healthy Children and in Those with Congenital Heart Disease Both Before and After Operation", The American Journal of Cardiology, vol. 83, pp.: 1654–1657 (Jun. 15, 1999).

Soejima MD, Kyoko et al., "Influence of Age on Ambulatory Electrocardiogram–derived Heart Rate Variability", Canadian Journal of Cardiology, vol. 15, No. 2, pp.: 142, 181–184, (Feb. 1999).

Gillette, MD, Paul C. et al., "Pediatric Cardiac Pacing", Cardiology Clinics, vol. 10, No. 4, pp.: 749–754 (Nov. 1992).

Davignon, Andre et al., "Normal ECG Standards for Infants and Children", Pediatric Cardiology, vol. 1, No. 2, pp.: 124–152 (1979/1980).

Primary Examiner—Scott M. Getzow

(57) ABSTRACT

A device for monitoring cardiac activity in pediatric patients and providing therapeutic stimuli to the pediatric patient such that the basic pacing rate of therapy provided varies so as to closely match the normal variation in a pediatric patient's normal heart rate. In one aspect, the device is initialized with the patient's age at implantation and, via time updates provided by a timer, changes the intrinsic rate of stimulation in accordance with an average heart rate for the patient's age. In another aspect, the device monitors a proxy signal indicative of the patient's age, such as the respiration rate via the minute respiration signal, and varies the intrinsic rate of stimulation in accordance with the proxy indicator of age. In this aspect, the intrinsic stimulation rate is set at a multiple of the respiration rate wherein the multiple is between 6 and 10.

32 Claims, 5 Drawing Sheets

PEDIATRIC RATE VARYING IMPLANTABLE CARDIAC DEVICE

FIELD OF THE INVENTION

The following invention relates to the field of implantable cardiac devices and, in particular, to an implantable cardiac device with an automatically varying pacing rate suitable for pediatric patients.

BACKGROUND OF THE INVENTION

The heart rate for adults is typically time invariant for given levels of activity and excitement and a normal relaxed, resting heart rate is on the order of 60–80 beats per minute (bpm). However, babies are normally born with a very high intrinsic resting heart rate compared to adults. It can often start as high as 120 bpm. The pediatric heart rate then typically climbs to a peak of approximately 150 bpm at two weeks of age, holds at approximately that rate for about two months, and then tapers off as the child ages until the heart rate reaches its adult level. It should be understood that children, like adults, experience normal instantaneous variation in heart rate due to sleep/wake cycles, eating, physical exertion, and the like.

Implantable cardiac devices, such as pacemakers and implantable cardioverter defibrillators, are known devices that are implanted in patients experiencing heart arrhythmias. Pacemakers typically monitor the beating of the heart and provide artificial stimulation to the heart to override brady/tachycardia and other arrhythmias. Implantable cardiac devices typically are programmed with a basic pacing rate and are set to deliver a pacing pulse of at least the basic pacing rate if the heart does not do so itself. Generally, implantable pacemakers include sensors that detect the intrinsic heart activity. They also include sensors that detect parameters indicative of the patients level of activity and metabolic need. These sensors can include activity sensors, transthoracic impedance sensors and the like that send signals to the control unit of the implantable cardiac stimulation device to ensure that the heart rate is maintained at a level consistent with the patient's activity.

With many patients, the implantable pacemaker is a demand-type pacemaker that only provides a pacing pulse when it detects the absence of an intrinsic heart event. In this way, the pacing is kept to a minimum. Hence, pacemakers are typically programmed with a basic pacing rate that can be adjusted upwards based upon the observed activity level and metabolic need of the patient. The basic pacing rate is thus used as a benchmark to determine when to apply a pacing pulse to the patient based upon the observed intrinsic activity of the patient.

Progress in reducing the size of pacemakers and other implantable cardiac stimulation devices has made them a feasible option for pediatric patients. Pediatric patients can have arrhythmias with observable characteristics similar to those seen in adults. Hence, pacemakers have been implanted in pediatric patients in order to regulate heart function. These pediatric pacemakers can include features and circuitry that allow for the delivery of demand-type pacing pulses and also allow for the adjustment of the pacing rate depending upon the activity and the metabolic need of the pediatric patient in a similar manner as described above.

However, the aforementioned variation in the child's intrinsic heart rate over time typically requires repeated adjustment of the pacemaker's intrinsic pacing rate by a physician. As discussed above, the pediatric patient's intrinsic heart rate is varying very significantly during the first several months of life. If the basic pacing rate is not adjusted, the pediatric patient heart may beat at a rate that is either too high or too low which can cause discomfort or even impair the health and development of the pediatric patient.

It will be appreciated that repeated visits to or by a physician are an inconvenient and expensive proposition for the patient and its family. As discussed above, the intrinsic heart rate of the pediatric patient can be varying significantly on a day-to-day basis requiring multiple trips to the physician during the first several weeks of life. These trips can be quite stressful for both the patient and the parents of the patient.

From the foregoing, it will be appreciated that there is a need for a pacemaker that is suitable for use with pediatric patients that requires less follow up visits. To this end, there is a need for a pediatric pacemaker that requires less adjustment after implantation.

SUMMARY OF THE INVENTION

The aforementioned needs are satisfied by the pediatric rate pacemaker of the present invention which includes one or more pacing leads that are positionable adjacent the heart of a pediatric patient and a pacing pulse generation circuit and control circuitry to control the delivery of pacing pulses to the heart of the pediatric patient. In one aspect, the control circuitry includes a microcontroller that is adapted to be able to adjust the basic pacing rate, which is the minimum rate at which pacing pulses will be provided to the patient in the absence of intrinsic heart activity, such that the basic pacing rate more closely corresponds to the changes in the intrinsic heart rate of an otherwise normal child during the first intervals of life.

In one implementation, a timer provides timing signals to the microprocessor such that the microprocessor receives signals indicative of the age of the pediatric patient. The microprocessor is further adapted to adjust the basic pacing rate such that, over time, the basic pacing rate more closely corresponds to the observed changes in the intrinsic heart rate of normal children of similar age.

In this implementation, the microcontroller is preferably configured to increase the basic pacing rate from a predetermined minimum to a predetermined maximum rate during a first interval of life. The microcontroller is then preferably configured to maintain the basic pacing rate near the maximum rate during a second interval of life and then gradually decrease the basic pacing rate from the maximum rate to a normal rate during a third interval of life.

In one embodiment, the first interval of life is between approximately 1 and 14 days and the beginning rate is approximately 120 bpm with the maximum rate being approximately 150 bpm. The second interval of life is approximately 60–80 days long wherein the basic pacing rate is maintained at a rate that is close to 150 bpm. The third interval of life is approximately 1000–1200 days long and the basic pacing rate is decreased to approximately 80 bpm which is the normal rate.

In one specific implementation, the basic pacing rate is adjusted through the first, second and third intervals by using a logarithmic best fit calculation that matches observed development of pediatric heart rates in normal pediatric patients. In one specific embodiment the basic pacing rate r is calculated according to the formula:

$$r=120.796-1.47035(\log(n))+35.1674(\log(n))^2-19.2293(\log(n))^3+2.47521(\log(n))^4$$

wherein r is the basic pacing rate and n is the age of the patient in number of days.

In another implementation, a physiologic characteristic of the pediatric patient is monitored and is used to determine whether to adjust the basic pacing rate. In one specific embodiment, the patient's respiration rate is monitored by periodic measurement of the transthoracic impedance. An average respiration rate is then periodically determined and is then used to determine whether the basic pacing rate needs to be adjusted.

The average respiration rate varies in a manner that is similar to the variation in the intrinsic heart rate of a pediatric patient over time. By measuring the average respiration rate, this data can either be used to adjust the basic pacing rate directly or it can be used to correlate the basic pacing rate determined by a formula based on age, such as the formula above, to thereby provide more accurate adjustment of the basic pacing rate. Other physiologic parameters, such as evolution of T-waves, can also be monitored and used to adjust the basic pacing rate to account for age development of the pediatric patient as the T-wave morphology is strongly correlated with the maturation stage.

Hence, the embodiments of the present invention provide for a pacing system that adjusts the basic pacing rate for the development of the pediatric patient. As the basic pacing rate is being automatically adjusted, fewer follow up visits to the physician are required and the pediatric patient receives pacing at a rate that is more consistent with the development of the heart of an otherwise normal child. These and other objects and advantages will become more apparent from the following description taken in conjunction with the accompanying drawings.

BRIEF DESCRIPTION OF THE DRAWINGS

Further features and advantages of the present invention may be more readily understood by reference to the following description taken in conjunction with the accompanying drawings, in which.

DETAILED DESCRIPTION OF THE PREFERRED EMBODIMENT

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
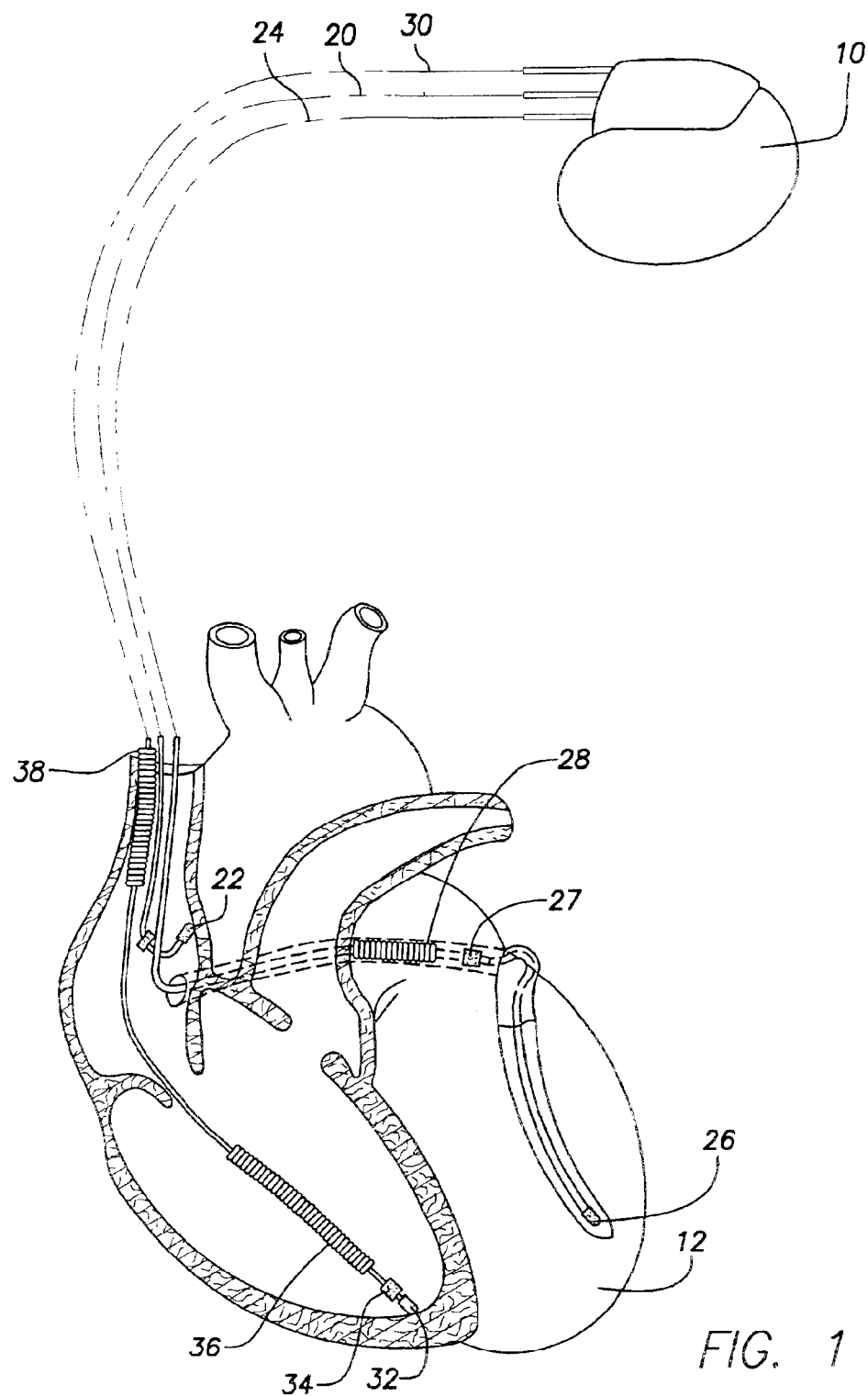
FIG. 1 is a simplified diagram illustrating an implantable stimulation device in electrical communication with at least three leads implanted into a patient's heart for delivering multi-chamber stimulation and shock therapy.

As shown in FIG. 1, there is a stimulation device 10 in electrical communication with a patient's heart 12 by way of three leads 20, 24 and 30 suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. For a complete description of a coronary sinus lead, see U.S. patent application Ser. No. 09/457,277, "A Self-Anchoring, Steerable Coronary Sinus Lead" (Pianca et al.), and U.S. Pat. No. 5,466,254, "Coronary Sinus Lead with Atrial Sensing Capability" (Helland), which patents are hereby incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals and delivering stimulation in the form of pacing and shock therapy to the right ventricle.

Figure 2:
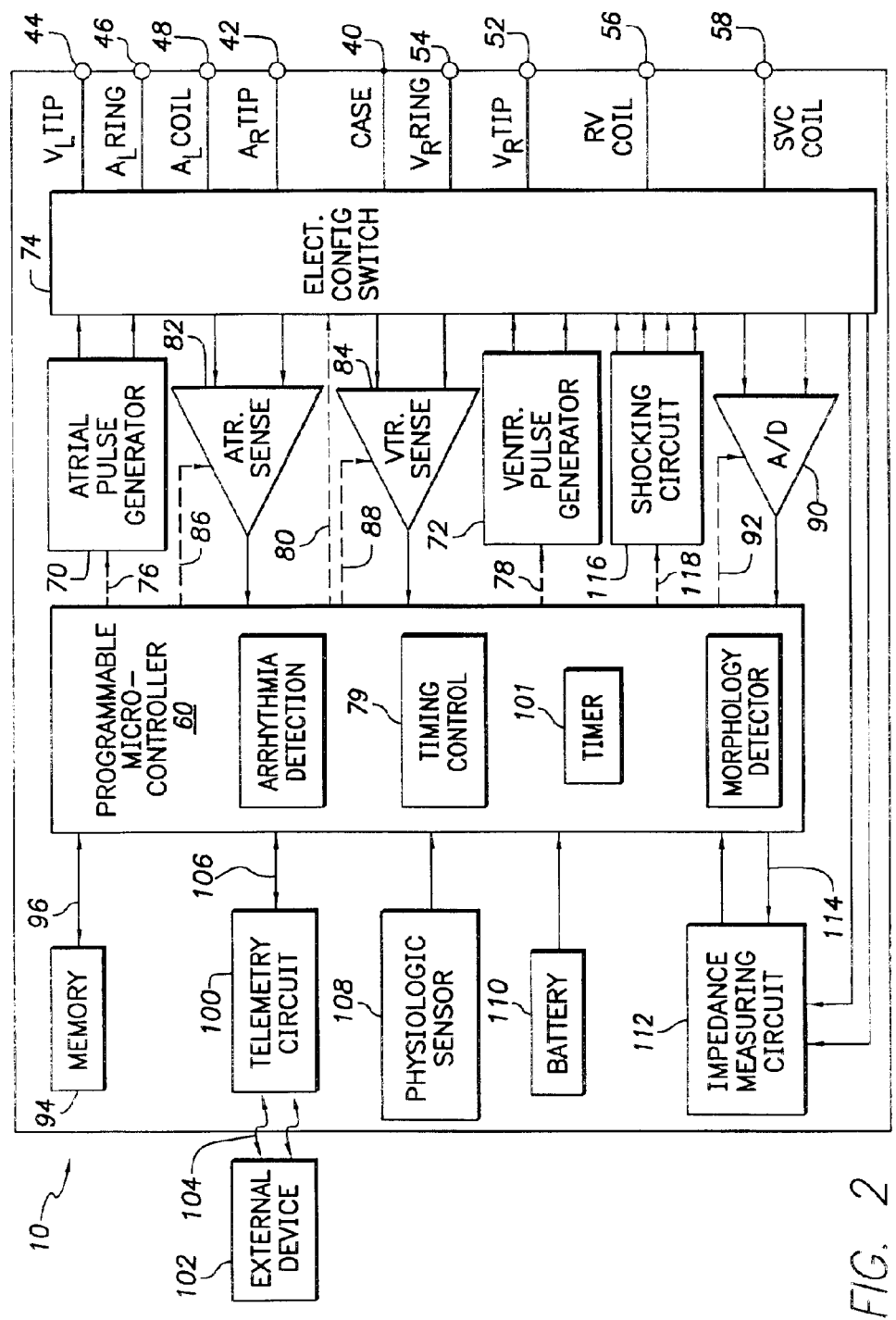
FIG. 2 is a functional block diagram of a multi-chamber implantable stimulation device illustrating the basic elements of a stimulation device which can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 27, the left atrial tip electrode 26, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. Any suitable microcontroller 60 may be used that carries out the functions described herein. The use of microprocessor-based control circuits for performing timing and data analysis functions are well known in the art.

As is also indicated in FIG. 2, the microcontroller 60 includes a timer 101 that is adapted to provide timing signals following implantation of the device 10. The timer 101 is logically implemented in any of a number of well known ways using the internal clock of the microcontroller 60 in a well known manner. As will be discussed below, the timer 101 provides timing signals that are used, in this implementation to adjust the basic pacing rate of the pediatric patient to account for the development of the pediatric patient's heart rate over time.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart 12, the atrial and ventricular pulse generators 70, 72 may include dedicated, independent pulse generators, multiplexed pulse generators, or shared pulse generators. The pulse generators 70, 72 are controlled by the microcontroller 60 via appropriate control signals 76, 78 respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, PVARP intervals, noise detection windows, evoked response windows, alert intervals, marker channel timing, etc., which is well known in the art.

The switch 74 includes a plurality of switches for connecting the desired electrodes to the appropriate 110 circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart 12. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifier with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, is able to trigger or inhibit the atrial and ventricular pulse generators, 70 and 72, respectively, in a demand fashion in response to the absence or presence of cardiac activity in the appropriate chambers of the heart 12. The sensing circuits, 82 and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sensing circuits, 82 and 84, as is known in the art.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

Advantageously, the data acquisition system 90 may be coupled to the microcontroller 60, or other detection circuitry, for detecting an evoked response from the heart 12 in response to an applied stimulus, thereby aiding in the detection of "capture". Capture occurs when an electrical stimulus applied to the heart 12 is of sufficient energy to depolarize the cardiac tissue, thereby causing the heart muscle to contract. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing control circuitry 79 within the microcontroller 60, and enabling the data acquisition system 90 via a control signal 92 to sample the cardiac signal that falls in the capture detection window and, based on the amplitude, determines if capture has occurred.

Capture detection may occur on a beat-by-beat basis or on a sampled basis. Preferably, a capture threshold search is performed once a day during at least the acute phase (e.g., the first 30 days) and less frequently thereafter. A capture threshold search would begin at a desired starting point (either a high energy level or the level at which capture is currently occurring) and decrease the energy level until capture is lost. The value at which capture is lost is known as the capture threshold. Thereafter, a safety margin is added to the capture threshold.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patients heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust the pacing stimulation rate according to the exercise state of the patient. However, the physiological sensor 108 may further be used to detect changes in cardiac output, changes in the physiological condition of the heart 12, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses. While shown as being included within the stimulation device 10, it is to be understood that the physiologic sensor 108 may also be external to the stimulation device 10, yet still be implanted within or carried by the a patient. A common type of rate responsive sensor is an activity sensor, such as an accelerometer or a piezoelectric crystal, which is mounted within the housing 40 of the stimulation device 10. Other types of physiologic sensors are also known, for example, sensors which sense the oxygen content of blood, respiration rate and/or minute ventilation, pH of blood, ventricular gradient, etc. However, any sensor may be used which is capable of sensing a physiological parameter which corresponds to the exercise state of the patient.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have predictable discharge characteristics so that elective replacement time can be detected. Accordingly, the device 10 preferably employs lithium/silver vanadium oxide batteries, as is true for most (if not all) current devices.

The stimulation device 10 further includes a magnet detection circuitry (not shown), coupled to the microcontroller 60. It is the purpose of the magnet detection circuitry to detect when a magnet is placed over the stimulation device 10, which magnet may be used by a clinician to perform various test functions of the stimulation device 10 and/or to signal the microcontroller 60 that the external programmer 102 is in place to receive or transmit data to the microcontroller 60 through the telemetry circuits 100.

As further shown in FIG. 2, the device 10 is shown as having an impedance measuring circuit 112 which is enabled by the microcontroller 60 via a control signal 114. The known uses for an impedance measuring circuit 112 include, but are not limited to, lead impedance surveillance during the acute and chronic phases for proper lead positioning or dislodgment, detecting operable electrodes and automatically switching to an operable pair if dislodgment occurs, measuring respiration or minute ventilation, measuring thoracic impedance for determining shock thresholds, detecting when the device has been implanted, measuring stroke volume, and detecting the opening of heart valves, etc. The impedance measuring circuit 112 is advantageously coupled to the switch 74 so that any desired electrode may be used.

In the case where the stimulation device 10 is intended to operate as an implantable cardioverter/defibrillator (ICD) device, it must detect the occurrence of an arrhythmia, and automatically apply an appropriate electrical shock therapy to the heart 12 aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38.

As noted above, the housing 40 may act as an active electrode in combination with the RV coil electrode 36, or as part of a split electrical vector using the SVC coil electrode 38 or the left atrial coil electrode 28 (i.e., using the RV coil electrode 36 as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
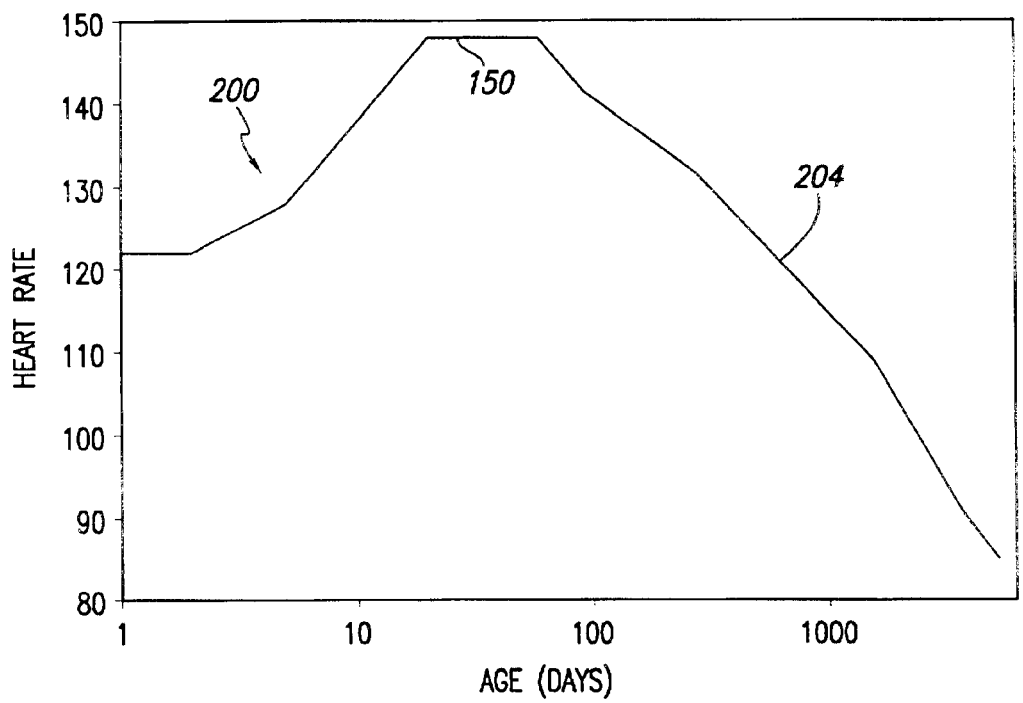
FIG. 3 is a graph that illustrates the development of a normal pediatric patient's heart rate during the first intervals of life.

FIG. 3 is a chart that illustrates the development of the intrinsic heart rate of a pediatric patient over time. As indicated, at birth, the typical pediatric patient has a heart rate on the order of 120 bpm. During a first interval, e.g., the first 14 or so days of life, the typical intrinsic heart rate is rising, as indicated by curve section 200, until it reaches a peak that is approximately 150 bpm. During a second interval, approximately the next 8–10 weeks, the heart rate stabilizes at the rate of approximately 150 bpm, as is indicated by the curve section 202. Subsequently, during a third interval, the rate decreases to the adult normal rate of approximately 80 bpm over the next 3 to 4 years as is indicated by the curve section 202 in FIG. 3.

In order for the pediatric patient to receive more appropriate pacing, it is desirable that the implanted device be programmed to provide pacing at a basic rate that generally tracks the curve in FIG. 3. In this way, the basic pacing rate more closely approximates what would be the intrinsic heart rate of the otherwise healthy pediatric patient. It is understood that the intrinsic heart rate varies in this manner as a result of the development of the child and, by more closely matching the basic pacing rate to the intrinsic heart rate of the otherwise healthy child, the patient's development is fostered.

As will be described in greater detail hereinbelow, the basic pacing rate can be adjusted over time to more closely approximate the curve of FIG. 3 either as a result of preprogramming the rate into the microcontroller 60 or by adjusting the rate after evaluation of another physiologic parameter of the patient that is indicative of age or some combination of these approaches. In one implementation, the basic pacing rate is adjusted over time by the microcontroller 60 according to a logarithmic function that is selected to generally match the shape of the curve shown in FIG. 3. In another implementation, the basic pacing rate is adjusted as a result of periodic observations of another physiologic parameter of the patient that also changes with age in a manner similar to the change in heart rate. For example, respiration rate also generally tracks the shape of the curve of FIG. 3 and can thus be used as an indicator of the age of the patient as will be described in greater detail hereinbelow. Similarly, the morphology of the T-wave can also provide an indication of the pediatric patients age.

Figure 4:
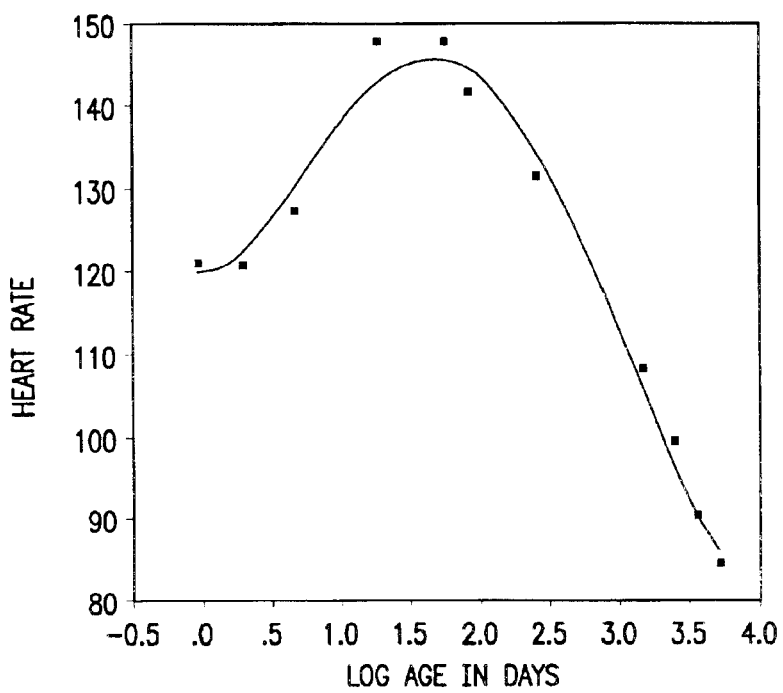
FIG. 4 is a graph illustrating one possible best fit curve to adjust the basic pacing rate over time to approximate the otherwise normal development of a pediatric patient's heart rate over time.

FIG. 4 is a chart illustrating a logarithmic curve that has been fitted to generally match the shape of the curve of FIG. 3. In this implementation, the curve is defined by the function:

$$r = 120.796 - 1.47035 (\log(n)) + 35.1674 (\log(n))^2 + 19.2293 (\log(n))^3 + 2.47521 (\log(n))^4 \quad (1)$$

wherein r is the basic pacing rate and n is the patient age in days. The function (1) is selected to provide a mathematical "best fit" to the observed characteristics of FIG. 3. As indicated, the curve defined by the function (1) is a $4^{th}$ order polynomial fit that provides a basic pacing rate that is generally increasing during a first interval, is generally constant during a second interval and is then generally decreasing during a third interval such that the basic pacing rate r defined by the function corresponds to the observed development of the intrinsic heart rate of an otherwise normal pediatric patient.

Figure 5:
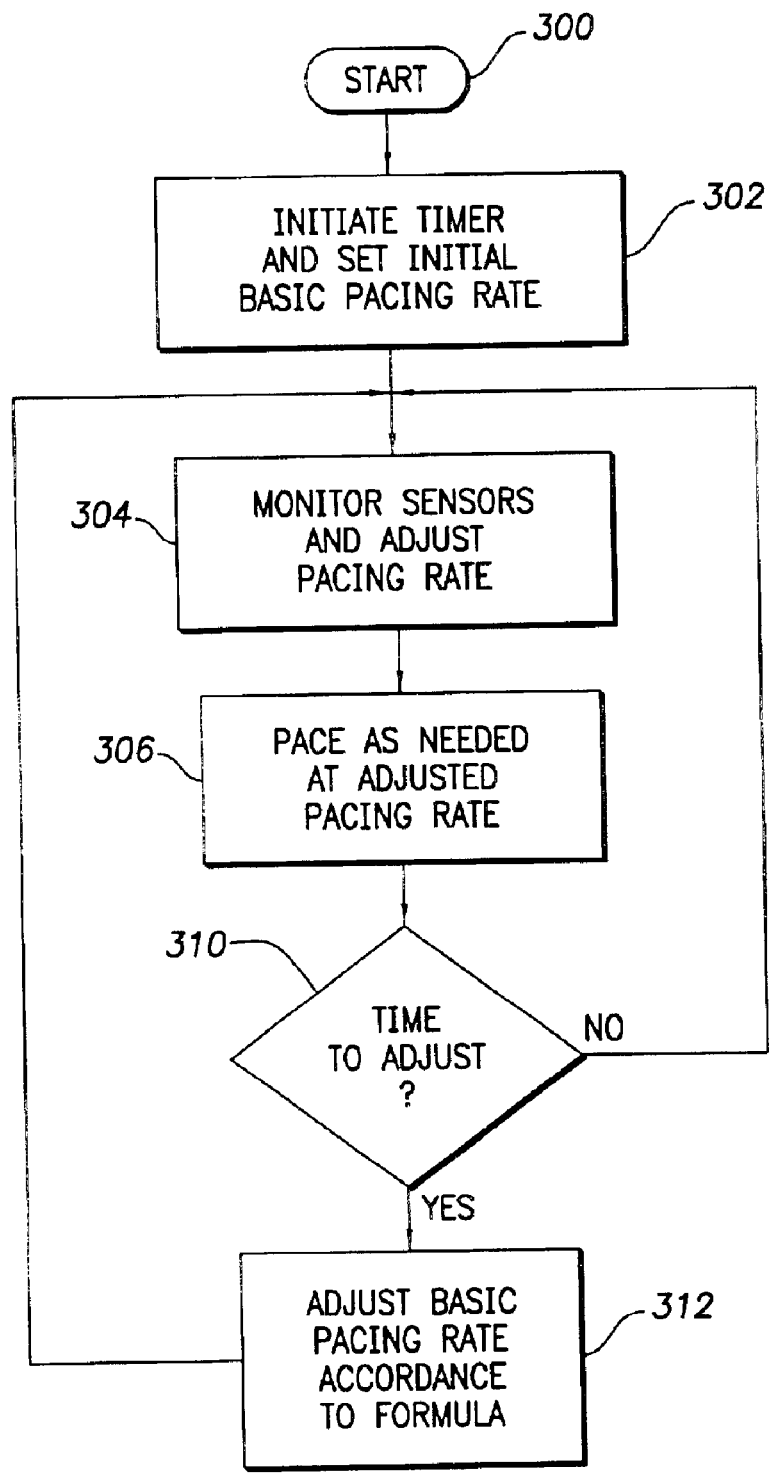
FIG. 5 is an exemplary flow chart illustrating one implementation of the cardiac device of FIGS. 1 and 2 as it adjusts the basic pacing rate of a pediatric patient.

FIG. 5 is a flow chart generally illustrating how the microcontroller 60 would provide pacing to the patient and also how the microcontroller 0.60 will adjust the basic pacing rate over time. It will be appreciated that FIG. 5 is simply exemplary of one possible manner in which pacing would be provided and is used for illustrative purposes only. As indicated in FIG. 5, the microcontroller 60 from a start state 300, initiates the timer 101 (FIG. 2) and sets an initial basic pacing rate in state 302. At implantation, the implanting physician initiates the implanted device which results in the microcontroller initiating the timer 101 in a known manner. The timer 101 is incremented by the internal clock of the programmable microcontroller 60. In this way, the microcontroller 60 knows the time since implantation of the pacemaker 10. At this point, the microcontroller 60 also is set with the initial basic pacing rate.

As discussed above, the basic pacing rate is the minimum pacing rate at which the device 10 will provide pacing pulses to the heart of the patient. This basic pacing rate will, of course, be adjusted in a known manner depending upon the sensed activity or the sensed metabolic need of the patient. Preferably, at implantation, the implanting physician or someone associated therewith, sets the initial basic rate at a rate that corresponds to the age of the pediatric patient according the curve of FIG. 3, e.g., at approximately 120 bpm. The timer 101 is also preferably set at that point such that the basic pacing rate can be adjusted along the curve of FIG. 4 regardless of when the pacemaker is actually implanted.

Once the device has been implanted and the timer and pacing rate has been set, the device 10 then begins to operate and provide pacing pulses to the patient as needed. In particular, the microcontroller in state 304 begins to monitor the sensors, such as the physiologic sensor 108 and the impedance measurement circuit 112 so as to determine the patient's activity and metabolic need. The microcontroller 60 then adjusts the pacing rate in a known manner. The microcontroller in state 306 then paces, as needed, at the adjusted pacing rate. It is understood that the pacemaker can be any of a number of different types of pacemakers including demand-type pacemakers wherein pacing pulses are only provided in the absence of an intrinsic event. In this circumstance, the adjusted pacing rate is the heart rate that the microcontroller 60 will attempt to maintain by providing pacing pulses as needed, e.g., in the absence of an intrinsic event.

The microcontroller 60 also periodically determines in state 310 whether it is time to adjust the basic pacing rate according to the function (1) above. As discussed above, the microcontroller 60 initiates a timer and at periodic intervals, e.g., daily, adjusts the basic pacing rate. The time to adjust decision is typically an interrupt that is sent to the microcontroller 60 as it is providing pacing pulses in states 304, 306. Once the microcontroller 60 determines that it is time to adjust the basic pacing rate, the microcontroller 60 calculates the new basic pacing rate 60 using the formula (1) and then returns to states 304 and 306 whereby pacing therapy is provided at the adjusted pacing rate.

Since the microcontroller 60 is programmed to periodically adjust the basic pacing rate according to the function (1), the microcontroller 60 is able to adjust the basic pacing rate to track the normal development of the heart rate of an otherwise healthy child. The function (1), is, in this implementation, a mathematical fit to the observed development of a normal child's heart rate and any of a number of formulas that are predictive of the development of a pediatric patient's heart rate over time can be used without departing from the spirit of the present invention.

Figure 6:
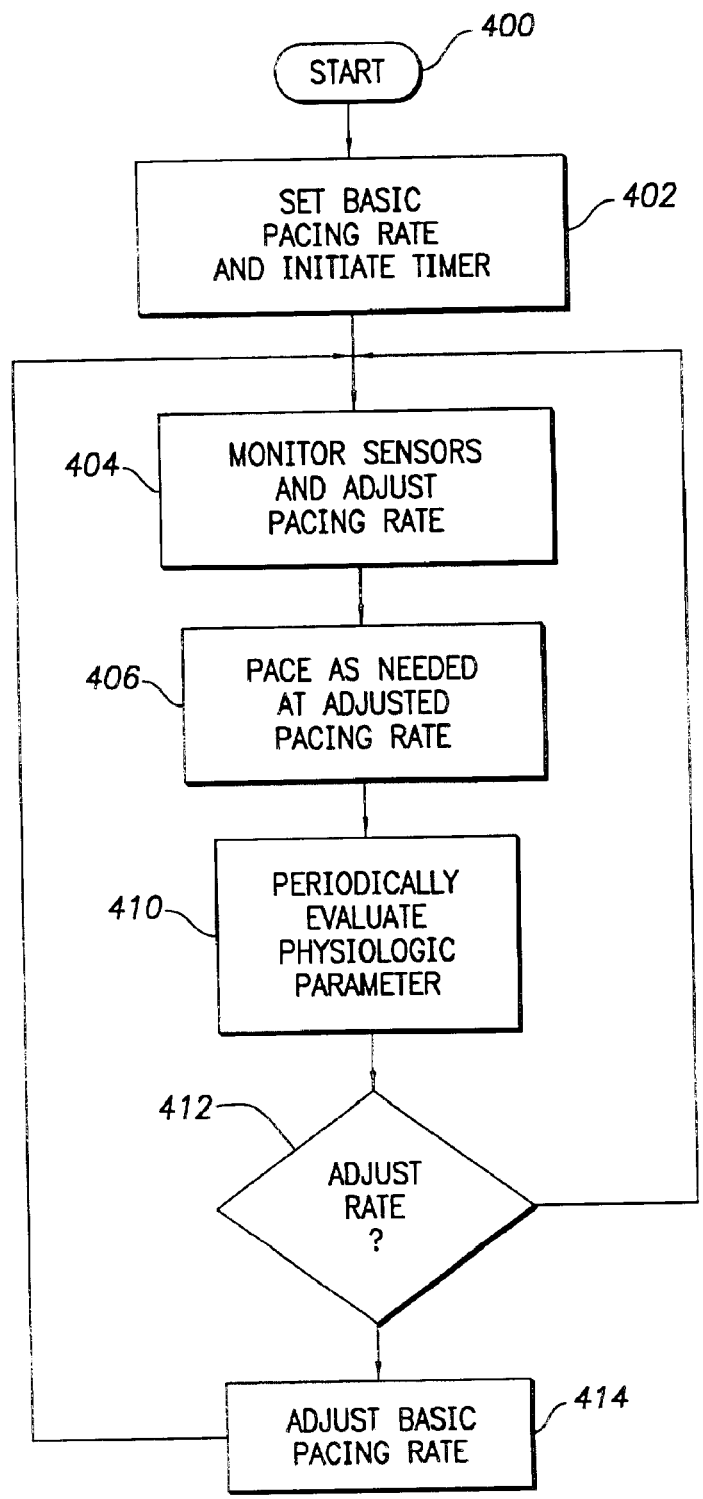
FIG. 6 is an exemplary flow chart illustrating another implementation of the cardiac device of FIGS. 1 and 2 as it adjusts the basic pacing rate of a pediatric patient.

FIG. 6 is a flow chart that illustrates an alternative manner of adjusting the basic pacing rate. It is understood that various other pediatric patient parameters are also adjusting during the first several weeks of life in a manner corresponding to the basic heart rate adjustment shown in FIG. 3. In particular, respiration rates generally track heart rates for pediatric patients. Consequently, it may be desirable to adjust the heart rate not only based upon a timer, but also by correlation with an observed physiologic parameter, such as respiration rate or T-wave morphology. As is known, respiration rates can be determined via minute ventilation measurements which are typically measured with implanted pacemakers via measurements of the transthoracic impedance. By correlating the measured respiration rate with the measured age of the pediatric patient, the basic pacing rate can potentially be more closely matched with the pediatric patient's actual development.

As indicated in FIG. 6, in this implementation, from a start state 400, the basic pacing rate is set and the timer 101 is initiated in state 402 in the same manner as described above. The microcontroller 60 then monitors the sensors and adjusts in state 404 the pacing rate from the basic pacing rate based upon the patient's activity and metabolic need in a known manner. Similarly, the microcontroller 60 induces the delivery of pacing pulses as needed in state 406 in the same manner as described above.

However, the microcontroller 60 is periodically receiving transthoracic impedance measurements from the impedance measurement circuit 112. As is understood, the transthoracic impedance measurement is indicative of respiration rate. The microcontroller 60 can accumulate sufficient measurements to be able to determine an average respiration rate for the pediatric patient. The average respiration rate can then be evaluated to determine where the particular pediatric patient is in terms of the development of their heart rate. The microcontroller 60, in this implementation, can then determine, in decision state 412, whether to adjust the basic pacing rate and can then adjust the basic pacing rate, in state 414, to account for the age of the pediatric patient and also the observed physiologic characteristics.

Hence, from the foregoing, it will be appreciated that the pediatric rate pacemaker of the illustrated embodiments allow for the basic pacing rate to be adjusted over time, or in response to an observed physiologic parameter, or some combination thereof, to more closely track the development of the pediatric patients heart rate over time. This can result in fewer visits to the physician's office for subsequent adjustment of the basic pacing rate and can also result in the pediatric patient receiving pacing therapy at a rate that more closely approximates the normal intrinsic heart rate of pediatric patients.

Although the preferred embodiments of the present invention have shown, described and pointed out the fundamental novel features of the invention as applied to those embodiments, it will be understood that various omissions, substitutions and changes in the form of the detail of the device illustrated may be made by those skilled in the art without departing from the spirit of the present invention. Consequently, the scope of the invention should not be limited to the foregoing description but is to be defined by the appended claims.

What is claimed is:

1. An implantable cardiac device adapted to be implanted in pediatric patients, the device comprising:
   at least one lead that is positionable adjacent a heart of the pediatric patient so as to be able to deliver pacing pulses thereto;
   a pulse generator that produces pacing pulses and provides the pacing pulses to the at least one lead; and
   a controller that controls the pulse generator to produce the pacing pulses, wherein the controller is configured to induce the delivery of pacing pulses to the heart at least at a basic pacing rate in the absence of any intrinsic heart activity, wherein the controller is further configured to adjust the basic pacing rate over time such that the basic pacing rate corresponds to an age related variation in an intrinsic heart rate of a normal child of a same age as the pediatric patient.

2. The device of claim 1, further comprising a sensor that detects when the heart is providing an intrinsic heartbeat and provides a signal indicative thereof, wherein the controller receives the signal and inhibits delivery of pacing pulses when intrinsic heartbeats occur.

3. The device of claim 1, further comprising a metabolic need, sensor that provides signals to the controller indicative of the metabolic need of the pediatric patient, wherein the controller induces the delivery of pacing pulses at an adjusted pacing rate greater than the basic pacing rate to accommodate the sensed metabolic need of the pediatric patient.

4. The device of claim 1, wherein the controller adjusts the basic pacing rate during a first time interval wherein the intrinsic heart rate of a normal child is increasing and wherein the controller maintains a substantially constant basic pacing rate during a second time interval wherein the intrinsic heart rate of a normal child is substantially constant and wherein the controller decreases the basic pacing rate during a third time interval wherein the intrinsic heart rate of a normal child is decreasing.

5. The device of claim 4, wherein the first interval comprises from the birth of the child until the child is approximately 14 days and wherein the controller adjusts the basic pacing rate from approximately 120 bpm to approximately 150 bpm.

6. The device of claim 5, wherein the second interval comprises from 14 days until approximately 60–80 days and wherein the controller maintains the basic pacing rate at approximately 150 bpm.

7. The device of claim 6, wherein the third interval comprises from approximately 75 days to 1000–1200 days and wherein the controller decreases the basic pacing rate from approximately 150 bpm to approximately 80 bpm.

8. The device of claim 4, wherein the controller monitors a timer and periodically adjusts the basic pacing rate in response to the timer.

9. The device of claim 4, wherein the controller monitors a body parameter of the pediatric patient that is indicative of age and adjusts the rate at least in part in response to the monitored body parameter.

10. The device of claim 9, further comprising a transthoracic impedance sensor that provides signals to the controller that allows the controller to determine a respiration rate and wherein the controller evaluates the respiration rate to determine the age of the pediatric patient.

11. A pediatric pacemaker device that is capable of being implanted in a pediatric patient, the device comprising:
   a pacing pulse delivery system that is adapted to generate and deliver pacing pulses to the patient; and a controller that induces the delivery of pacing pulses to the pediatric patient, wherein the controller induces the delivery of pacing pulses at an adjustable pacing rate;

wherein the adjustable pacing rate is automatically adjusted over time based on the age of the patient; and wherein the controller induces the delivery of pacing pulses to the patient at least at a basic pacing rate, in the absence of intrinsic heart activity and wherein the controller adjusts the basic pacing rate over time such that the basic pacing rate adjusts to correspond to the typical variation in intrinsic heart rates of a normal child of the same age as the pediatric patient.

12. The device of claim 11, further comprising a sensor that detects when the heart is providing an intrinsic heartbeat and provides a signal indicative thereof, wherein the controller receives the signal and inhibits delivery of pacing pulses when intrinsic heartbeats occur.

13. The device of claim 11, further comprising a metabolic need sensor that provides signals to the controller indicative of the metabolic need of the pediatric patient, wherein the controller induces the delivery of pacing pulses at an adjusted pacing rate greater than the basic pacing rate to accommodate the sensed metabolic need of the pediatric patient.

14. The device of claim 11, wherein the controller adjusts the basic pacing rate during a first time interval wherein the intrinsic heart rate of a normal child is increasing and wherein the controller maintains a substantially constant basic pacing rate during a second time interval wherein the intrinsic heart rate of a normal child is substantially constant and wherein the controller decreases the basic pacing rate during a third time interval wherein the intrinsic heart rate of a normal child is decreasing.

15. The device of claim 14, wherein the first interval comprises from the birth of the child until the child is approximately 14 days and wherein the controller adjusts the basic pacing rate from approximately 120 bpm to approximately 150 bpm.

16. The device of claim 15, wherein the second interval comprises from 14 days until approximately 60–80 days and wherein the controller maintains the basic pacing rate at approximately 150 bpm.

17. The device of claim 16, wherein the third interval comprises from approximately 75 days to 1000–1200 days and wherein the controller decreases the basic pacing rate from approximately 150 bpm to approximately 80 bpm.

18. The device of claim 14, wherein the controller monitors a timer and periodically adjusts the basic pacing rate in response to the timer.

19. The device of claim 14, wherein the controller monitors a body parameter of the pediatric patient that is indicative of age and adjusts the rate at least in part in response to the monitored body parameter.

20. The device of claim 19, further comprising a transthoracic impedance sensor that provides signals to the controller that allows the controller to determine a respiration rate and wherein the controller evaluates the respiration rate to determine the age of the pediatric patient.

21. An implantable cardiac stimulation device, adapted to be implanted in a pediatric patient, the device comprising:

means for generating pacing pulses to be delivered to a heart of the pediatric patient; and control means for controlling the delivery of pacing pulses to the heart of the pediatric patient, wherein the control means induces the delivery of pacing pulses at an adjustable rate wherein the rate is adjusted based on the age of the pediatric patient so that the pediatric patient has a heart rate that varies to correspond with age-based variations in an intrinsic heart rate of a normal child.

22. The device of claim 21, wherein the control means induces the delivery of pacing pulses to the patient at least at a basic pacing rate, in the absence of intrinsic heart activity and wherein the control means adjusts the basic pacing rate over time such that the basic pacing rate adjusts to correspond to the typical variation in intrinsic heart rates of a normal child of the same age as the pediatric patient.

23. The device of claim 22, further comprising a sensor that detects when the heart is providing an intrinsic heartbeat and provides a signal indicative thereof, wherein the control means receives the signal and inhibits delivery of pacing pulses when intrinsic heartbeats occur.

24. The device of claim 23, further comprising a metabolic need sensor that provides signals to the control means indicative of the metabolic need of the pediatric patient, wherein the control means induces the delivery of pacing pulses at an adjusted pacing rate greater than the basic pacing rate to accommodate the sensed metabolic need of the pediatric patient.

25. The device of claim 22, wherein the control means adjusts the basic pacing rate during a first time interval wherein the intrinsic heart rate of a normal child is increasing and wherein the control means maintains a substantially constant basic pacing rate during a second time interval wherein the intrinsic heart rate of a normal child is substantially constant and wherein the control means decreases the basic pacing rate during a third time interval wherein the intrinsic heart rate of a normal child is decreasing.

26. The device of claim 25, wherein the first interval comprises from the birth of the child until the child is approximately 14 days and wherein the control means adjusts the basic pacing rate from approximately 120 bpm to approximately 150 bpm.

27. The device of claim 26, wherein the second interval comprises from 14 days until approximately 60–80 days and wherein the control means maintains the basic pacing rate at approximately 150 bpm.

28. The device of claim 27, wherein the third interval comprises from approximately 75 days to 1000–1200 days and wherein the control means decreases the basic pacing rate from approximately 150 bpm to approximately 80 bpm.

29. The device of claim 22, wherein the control means monitors a timer and periodically adjusts the basic pacing rate in response to the timer.

30. The device of claim 22, wherein the control means monitors a body parameter of the pediatric patient that is indicative of age and adjusts the rate at least in part in response to the monitored body parameter.

31. The device of claim 30, further comprising a transthoracic impedance sensor that provides signals to the controller that allows the control means to determine a respiration rate and wherein the control means evaluates the respiration rate to determine the age of the pediatric patient.

32. In an implantable cardiac stimulation device, a method of pacing a heart of a pediatric patient the method comprising:

setting a pacing rate based on the age of the pediatric patient; and on at least one subsequent occasion, automatically adjusting the pacing rate based on an updated age of the pediatric patient so that the pediatric patient has a heart rate that varies to correspond with age-based variations in an intrinsic heart rate of a normal child.

* * * * *